United States Patent
Schoepgens et al.

(10) Patent No.: US 10,456,606 B2
(45) Date of Patent: Oct. 29, 2019

(54) DECOLORIZATION OF COLORED KERATINIC FIBERS

(71) Applicant: Henkel AG & Co. KGaA, Duesseldorf (DE)

(72) Inventors: Juergen Schoepgens, Schwalmtal (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 104 days.

(21) Appl. No.: 15/400,984

(22) Filed: Jan. 7, 2017

(65) Prior Publication Data

US 2017/0113071 A1 Apr. 27, 2017

Related U.S. Application Data

(63) Continuation of application No. PCT/EP2015/063139, filed on Jun. 12, 2015.

(30) Foreign Application Priority Data

Jul. 9, 2014 (DE) .................. 10 2014 213 317

(51) Int. Cl.
*A61Q 5/08* (2006.01)
*A61K 8/34* (2006.01)
*A61K 8/60* (2006.01)
*A61K 8/36* (2006.01)
*A61K 8/19* (2006.01)
*A61K 8/41* (2006.01)
*A61K 8/49* (2006.01)
*A61K 8/44* (2006.01)
*A61K 8/45* (2006.01)
*A61K 8/46* (2006.01)

(52) U.S. Cl.
CPC .............. *A61Q 5/08* (2013.01); *A61K 8/19* (2013.01); *A61K 8/342* (2013.01); *A61K 8/347* (2013.01); *A61K 8/36* (2013.01); *A61K 8/411* (2013.01); *A61K 8/442* (2013.01); *A61K 8/45* (2013.01); *A61K 8/466* (2013.01); *A61K 8/4926* (2013.01); *A61K 8/4973* (2013.01); *A61K 8/602* (2013.01)

(58) Field of Classification Search
None
See application file for complete search history.

(56) References Cited

U.S. PATENT DOCUMENTS 6,379,657 B1 4/2002 Lorenz et al.
8,753,408 B2 6/2014 Emmerling et al.

FOREIGN PATENT DOCUMENTS

| DE | 102006022274 A1 | 11/2007 | |
|---|---|---|---|
| EP | 1300136 A2 | 4/2003 | |
| WO | 2008/055756 A1 | 5/2008 | |
| WO | WO-2013017862 A2 * | 2/2013 | ............... A61K 8/22 |
| WO | WO-2014174230 A2 * | 10/2014 | ............... A61K 8/22 |

OTHER PUBLICATIONS

PCT International Search Report (PCT/EP2015/063139) dated Aug. 26, 2015.

* cited by examiner

*Primary Examiner* — Nicole P Babson
(74) *Attorney, Agent, or Firm* — P. Scott Smith

(57) ABSTRACT

A multi-component packaging unit and related method for the reductive decolorization of colored keratinic fibers comprising, packaged separately from one another, (I) a container (A) containing a cosmetic agent (a),
(II) a container (B) containing a cosmetic agent (b), and
(III) a container (C) containing a cosmetic, aqueous agent (c), with
  the agent (b) in container (B) containing
    (a1) one or more reducing agents from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thio sulfate, ammonium thio sulfate, hydroxymethane sulfinic acid, aminomethane sulfinic acid, cysteine, thiolactic acid, sulfanylacetic acid (thioglycolic acid) and/or ascorbic acid, and
  agent (c) in container (C) including
    (c1) one or more acids from the group of the inorganic and/or organic acids and
    (c2) one or more zwitterionic and/or amphoteric surfactants.

12 Claims, No Drawings

DECOLORIZATION OF COLORED KERATINIC FIBERS

FIELD OF THE INVENTION

The present invention generally relates to multi-component packaging units (kits of parts) for the reductive decolorization of colored keratinic fibers, with the multi-component packaging units comprising containers (A), (B) and (C) that are packaged separately from one another. The container (A) contains a cosmetic agent (a) with at least one selected reducing agent, container (B) contains a cosmetic agent (b) that acts as a carrier, and container (C) contains an aqueous cosmetic agent (c) with at least one inorganic and/or organic acid and at least one zwitterionic and/or amphoteric surfactant. Another object of the object of the present invention is a method for the reductive decolorization of colored keratin fibers in which the previously described multi-component packaging unit is used.

BACKGROUND OF THE INVENTION

Preparations for tinting and coloring hair are an important type of cosmetic agent. They can be used for more or less pronounced shading of the natural hair color depending on the individual's desires, for achieving a completely different hair color, or for covering unwanted color tones, such as shades of gray, for example. Depending on the desired color or permanence of the coloration, common hair dyes are based either on oxidation dyes or on direct dyes. Combinations of oxidation dyes and direct dyes are also frequently used in order to achieve special nuances.

Coloring agents that are based on oxidation dyes result in brilliant and permanent color tones. However, they require the use of strong oxidizing agents such as hydrogen peroxide solutions, for example. Such coloring agents include oxidation dye precursors—so-called developer components and coupler components. The developer components form the actual dyes under the influence of oxidizing agents or atmospheric oxygen among one another or under coupling with one or more coupler components.

Coloring agents that are based on direct dyes are often used for temporary coloration. The direct dyes are dye molecules that are applied directly to the hair without the need for any oxidative processes to produce the color.

Some important representatives of this class of dyes are triphenylmethane dyes, azo dyes, anthraquinone dyes or nitrobenzene dyes, each of which can carry cationic or anionic groups.

With all of these coloration processes, the situation can arise in which, for any of various reasons, the coloration needs to be undone completely or partially. The partial removal of the coloration is expedient, for example, if the coloring result on the fibers turns out to be darker than desired. On the other hand, the complete removal of the coloration can be desired in some cases. For instance, it may be desired to color or tint the hair with a certain nuance for a specific occasion and to restore the original color after several days.

Means and methods for color removal are already known from the literature. One method for reversing coloration that is sufficiently known from the prior art is the oxidative decolorization of colored hair, for example with the aid of a common bleaching agent. In that process, however, the fibers can be damaged as a result of the use of strong oxidizing agents. Furthermore, reductive processes for color removal have also already been described. For example, European patent application EP 1300136 A2 discloses a hair treatment method in which the hair is colored in a first step and decolorized again reductively in a second step. Here, the reductive decolorization is performed using a formulation including a dithionite salt and a surfactant. In WO 2008/055756 A2, the reductive decolorization of keratin fibers is performed using a mixture of a reducing agent and an absorbing agent.

When using reductive decolorizing agents, the decolorization occurs through the reduction of the dyes located on the keratin fibers or hair. As a result of the reduction, the dyes are generally converted to their reduced leuko form. During this process, the double bonds present in the dyes are reduced, thereby interrupting the chromophoric system of the dyes and converting the dyes into a colorless form.

One general problem with the reductive decolorizing agents known from the prior art is that, while the colored keratin fibers can be decolorized using the reducing agent, the color removal is not permanent. Particularly in the case of oxidatively colored hair in which the coloration is produced on the hair through oxidation dye precursors of the developer and coupler type, colorations having very good fastness characteristics are obtained in part. When using the reductive decolorizing agent, these dyes are now converted reductively into uncolorized compounds—which, however, due to their similarly good fastness characteristics, remain on the hair.

After rinsing-off of the reducing agent, and under the effect of atmospheric oxygen, these reduced forms can be gradually reoxidized. This reoxidation results in a more or less pronounced recoloring. This recoloring generally does not match the color tone in which the keratin fibers were previously colored, but rather can be unattractive and is therefore all the less desirable for the user of the decolorizing agent.

It was therefore the object of the present invention to provide a decolorizing agent for decolorizing colored keratinic fibers that decolorizes colored keratinic fibers in a maximally complete manner. This decolorization should be long-lasting, and the decolorized keratin fibers should not experience any recoloration, nuance shift, or darkening under the effect of atmospheric oxygen. The decolorizing agent should exhibit good decolorization performance particularly on keratin fibers that were previously colored using oxidative colorants based on developer- and coupler-type oxidation dye precursors.

Surprisingly, it was found that the redarkening occurring after application of the reductive decolorizing agent can be effectively suppressed if the reductively decolorized keratin fibers are treated again with a post-treatment agent after decolorization that includes one or more acids from the group of the inorganic and/or organic acids and one or more zwitterionic and/or amphoteric surfactants.

Furthermore, other desirable features and characteristics of the present invention will become apparent from the subsequent detailed description of the invention and the appended claims, taken in conjunction with this background of the invention.

BRIEF SUMMARY OF THE INVENTION

Multi-component packaging unit (kit of parts) for the reductive decolorization of colored keratinic fibers comprising, packaged separately from one another, (I) a container (A) containing a cosmetic agent (a); (II) a container (B) containing a cosmetic agent (b); and (III) a container (C) containing a cosmetic, aqueous agent (c); with the agent (a)

in container (A) including (a1) one or more reducing agents from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethane sulfinic acid, aminomethane sulfinic acid, cysteine, thiolactic acid, sulfanylacetic acid (thioglycolic acid) and/or ascorbic acid; and agent (c) in container (C) including (c1) one or more acids from the group of the inorganic and/or organic acids; and (c2) one or more zwitterionic and/or amphoteric surfactants.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first object of the present invention is a multi-component packaging unit (kit of parts) for the reductive decolorization of colored keratinic fibers comprising, packaged separately from one another,
(I) a container (A) containing a cosmetic agent (a),
(II) a container (B) containing a cosmetic agent (b), and
(III) a container (C) containing a cosmetic, aqueous agent (c), with
the agent (a) in container (A) including
(a1) one or more reducing agents from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethane sulfinic acid, aminomethane sulfinic acid, cysteine, thiolactic acid, sulfanylacetic acid (thioglycolic acid) and/or ascorbic acid, and
agent (c) in container (C) including
(c1) one or more acids from the group of the inorganic and/or organic acids and
(c2) one or more zwitterionic and/or amphoteric surfactants.

The multi-component packaging unit according to the invention comprises containers (A) and (B), which are packaged separately from one another and each of which includes agents (a) and (b). Agent (a) includes at least one reducing agent (a1). Agent (b) is a carrier formulation that can be formulated so as to be water-containing or water-free. The ready-to-use decolorizing agent is prepared by mixing the two agents (a) and (b)—that is, by mixing reducing agent-containing agent (a) with the carrier (b).

Moreover, the multi-component packaging unit according to the invention comprises a third separately packaged container (C) with an agent (c). Agent (c) is a post-treatment agent that is to be applied after the application of the ready-to-use decolorizing agent onto the keratin fibers. By treating the keratin fibers immediately after decolorization, i.e., immediately after the ready-to-use decolorizing agent is applied, allowed to act, and rinsed out, the decolorization can be rendered more effective and, in particular, the reoxidation that leads to darkening can be effectively prevented.

It was particularly surprising to find that, when the multi-component packaging unit according to the invention is used, the decolorizing effect is extremely long-lasting and that even decolorized keratin fibers that are exposed to atmospheric oxygen for hours or days do not experience any reoxidation or darkening.

Keratinic fibers, keratin-containing fibers or keratin fibers are to be understood as furs, wool, feathers and, particularly, human hair. Even though the agents according to the invention are suitable first and foremost for lightening and coloring keratin fibers or human hairs, there is nothing in principle to prevent them from being used in other areas as well.

The term "colored keratinic fiber" is understood as referring to keratin fibers that were colored using conventional cosmetic colorants known to a person skilled in the art. Particularly, "colored keratinic fibers" are to be understood as fibers that have been colored using oxidative colorants and/or direct dyes known from the prior art. Express reference is made in this connection to the known monographs, e.g., to Kh. Schräder, *Grundlagen and Rezepturen der Kosmetika* [Fundamentals and Formulations of Cosmetics], 2nd edition, Hilthig Buch Verlag, Heidelberg, 1989, which reflect the corresponding knowledge of a person skilled in the art. The agents preferably include the ingredients essential to the invention in a cosmetic carrier (agents (a) and (b)) or in an aqueous cosmetic carrier (agent (c)). This can be a suitable aqueous or aqueous-alcoholic carrier, for example. For the purpose of reductive decolorization, such carriers can, for example, creams, emulsions, gels or even surfactant-containing foaming solutions such as shampoos, foaming aerosols, foam formulations or other preparations that are suitable for use on the hair. The agents for the reductive removal of color from keratinic fibers are especially preferably creams, emulsions or flowable gels.

Agent (a) can particularly also be packaged in a water-free manner and be present in solid form as a powder or paste, for example. Moreover, agent (a) can also comprise a solvent-containing carrier or a carrier made up of fat components such as fatty alcohols, fatty acid esters, hydrocarbons, silicone oils and/or hydrophobic oils, for example.

Agent (a) in Container (A)

The multi-component packaging unit according to the invention (kit of parts) comprises a first separately packaged container (A) with a cosmetic agent (a). Agent (a) is characterized in that it includes, as the first ingredient (a1) essential to the invention, at least one reducing agent from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethane sulfinic acid, aminomethane sulfinic acid, cysteine, thiolactic acid, sulfanylacetic acid (thioglycolic acid) and/or ascorbic acid. Sodium dithionite is an inorganic reducing agent with the empirical formula $Na_2S_2O_4$ and CAS no. 7775-14-6.

Zinc dithionite is an inorganic reducing agent with the empirical formula $ZnS_2O_4$ and CAS no. 7779-86-4.

Potassium dithionite is an inorganic reducing agent with the empirical formula $K_2S_2O_4$ and CAS no. 14293-73-3.

Sodium sulfite is an inorganic reducing agent with the empirical formula $Na_2SO_3$ and CAS no. 7757-83-7.

Sodium hydrogen sulfite is an inorganic reducing agent with the empirical formula $NaHSO_3$ and CAS no. 7631-90-5. Sodium hydrogen sulfite is preferably used in the form of an aqueous solution.

Potassium sulfite is an inorganic reducing agent with the empirical formula $K_2SO_3$ and CAS no. 10117-38-1.

Potassium hydrogen sulfite is an inorganic reducing agent with the empirical formula KHSO₃ and CAS no. 7773-03-7. Potassium hydrogen sulfite is preferably used in the form of an aqueous solution.

Ammonium sulfite is an inorganic reducing agent with the empirical formula $(NH_4)_2SO_3$ and CAS no. 10196-04-0.

Sodium thiosulfate is an inorganic reducing agent with the empirical formula $Na_2S_2O_3$ and CAS no. 7772-98-7.

Potassium thiosulfate is an inorganic reducing agent with the empirical formula $K_2S_2O_3$ and CAS no. 10294-66-3.

Ammonium thiosulfate is an inorganic reducing agent with the empirical formula $(NH_4)_2S_2O_3$ and CAS no. 7783-18-8.

Hydroxymethane sulfinic acid is an organic reducing agent with the empirical formula HO—CH₂—S(O)OH and CAS no. 79-25-4. Hydroxymethane sulfinic acid is alternatively also referred to as formaldehyde sulfoxylic acid. The use of hydroxymethane sulfinic acid itself and the use of the physiologically acceptable salts of hydroxymethane sulfinic acid, for example the sodium salt and/or zinc salt, is in keeping with the invention. The use of sodium formaldehyde sulfoxylate (sodium hydroxymethane sulfinate, the sodium salt of hydroxymethane sulfinic acid) and/or zinc formaldehyde sulfoxylate (zinc hydroxymethane sulfinate, the zinc salt of hydroxymethane sulfinic acid) is also in keeping with the invention.

Aminomethane sulfinic acid is an organic reducing agent with the formula H₂N—CH₂—S(O)OH and CAS no. 118201-33-5. Both the use of aminomethane sulfinic acid itself and the use of the physiologically acceptable salts of aminomethane sulfinic acid, for example the sodium salt and/or zinc salt, are in keeping with the invention. The use of sodium aminomethane sulfinate (the sodium salt of aminomethane sulfinic acid) and/or zinc aminomethane sulfinate (the zinc salt of aminomethane sulfinic acid) is therefore also in keeping with the invention.

Cysteine (2-amino-3-sulfanylpropionic acid) is understood according to the invention as being D-cysteine, L-cysteine and/or a mixture of D- and L-cysteine.

Thiolactic acid (2-sulfanylpropionic acid) is understood as being D-thio-lactic acid, L-thio-lactic acid and/or a mixture of D- and L-thiolactic acid. Both the use of thiolactic acid itself and the use of thiolactic acid in the form of a physiologically acceptable salt thereof are in keeping with the invention. One preferred salt of thiolactic acid is ammonium thiolactate.

Ammonium thiolactate is the ammonium salt of thiolactic acid (i.e., the ammonium salt of 2-sulfanylpropionic acid) (formula XX).

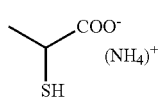
(Formula XX)

The definition of ammonium thiolactate also includes both the ammonium salts of D-thiolactic acid and the ammonium salts of L-thiolactic acid, as well as mixtures thereof. Sulfanylacetic acid (thioglycolic acid, 2-mercaptoacetic acid) is understood as being an organic reducing agent of the formula HS—CH₂—COOH having CAS no. 68-11-1. With thioglycolic acid as well, both the use of thioglycolic acid itself and the use of a physiologically acceptable salt of thioglycolic acid are in keeping with the invention. Some examples of physiologically acceptable salts of thioglycolic acid that can be used are sodium thioglycolate, potassium thioglycolate and/or ammonium thioglycolate. Ammonium thioglycolate is a preferred physiologically acceptable salt of thioglycolic acid.

Ammonium thioglycolate is the ammonium salt of thioglycolic acid (i.e., the ammonium salt of sulfanylacetic acid) (formula XXX).

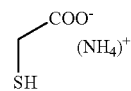
(Formula XXX)

According to the invention, ascorbic acid is understood particularly as referring to (R)-5-[(S)-1,2-dihydroxyethyl]-3,4-dihydroxy-5H-furan-2-on (other alternative names: vitamin C, L-ascorbic acid) with CAS no. 50-81-7.

The reducing agents sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate and/or ammonium thiosulfate have proven to be especially well suited for the reductive decolorization of oxidatively colored hair. If the abovementioned preferred reducing agents (a1) were post-treated with an agent (c) including the inventive combination of acids (c1) and the amphoteric or zwitterionic surfactants (c2), especially effective decolorization was achieved, and reoxidation in the decolorized strands of hair was prevented in an especially effective manner. In this way, darkening of the decolorized keratin fibers was able to be prevented over an especially long period of time.

Moreover, the reducing agent(s) from group (a) is/are used in certain quantity ranges. In order to achieve an optimal decolorizing effect, it is preferred if the decolorizing agent includes the reducing agent(s) (a1) in a total quantity of 25.0 to 100 wt %, preferably 45.0 to 100 wt %, more preferably 65.0 to 100 wt %, and especially preferably 85.0 to 100 wt % with respect to the total weight of agent (a).

An especially preferred multi-component packaging unit (kit of parts) is further characterized in that
the agent (a) in container (A) includes
(a1) one or more reducing agents from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate and/or ammonium thiosulfate in a total quantity of 25.0 to 100 wt %, preferably 45.0 to 100 wt %, more preferably 65.0 to 100 wt %, and especially preferably 85.0 to 100 wt % with respect to the total weight of agent (a).

A multi-component packaging unit (kit of parts) for the reductive decolorization of colored keratinic fibers is also especially preferred which is characterized in that
the agent (b) in container (B) including
(a1) one or more reducing agents from the group of sodium dithionite, zinc dithionite, potassium dithionite, sodium thiosulfate, potassium thiosulfate and/or ammonium thiosulfate in a total quantity of 25.0 to 100 wt %, preferably 45.0 to 100 wt %, more preferably 65.0 to 100 wt %, and especially preferably 85.0 to 100 wt % with respect to the total weight of agent (a).

Moreover, it has proven to be especially advantageous if the agents according to the invention include certain combinations of reducing agents from group (a1), since an especially strong decolorizing effect occurs with certain combinations. The use of two different reducing agents from group (a1) is especially advantageous in this connection, with the decolorizing agent including (a11) a first reducing agent that is selected from the group of sodium dithionite, zinc dithionite, potassium dithionite, sodium thiosulfate, potassium thiosulfate and/or ammonium thiosulfate, and, in addition, (a12) a second reducing agent that is selected from the group of sodium sulfite, sodium hydrogen sulfite, potassium sulfite, potassium hydrogen sulfite and/or ammonium sulfite.

In other words, a multi-component packaging unit for the reductive decolorization of colored keratinic fibers, particularly human hairs, is especially preferred in the context of this embodiment in which the agent (b) in container (B) including (a11) a first reducing agent that is selected from the group of sodium dithionite, zinc dithionite, potassium dithionite, sodium thiosulfate, potassium thiosulfate and/or ammonium thiosulfate, and, in addition, (a12) a second reducing agent that is selected from the group of sodium sulfite, sodium hydrogen sulfite, potassium sulfite, potassium hydrogen sulfite and/or ammonium sulfite.

Agent (b) in Container (B)

The multi-component packaging unit according to the invention comprises a second separately packaged container (B) containing an agent (b). This agent (b) is a cosmetic carrier formulation that can be preferably formulated so as to be aqueous or aqueous-alcoholic. Agent (b) is very especially preferably aqueous.

A very especially preferred multi-component packaging unit (kit of parts) is further characterized in that the agent (b) in container (B)

(b1) includes water.

Shortly before the decolorizing process, agents (a) and (b) are mixed to prepare the ready-to-use decolorizing agent.

Agent (b) is preferably prepared as a liquid preparation to which other surface-active substances can be added. They are preferably selected from among anionic, zwitterionic, amphoteric and nonionic surfactants and emulsifiers.

As anionic surfactants, agent (b) can include fatty acids, alkyl sulfates, alkyl ether sulfates, and ether carboxylic acids with 10 to 20 C-atoms in the alkyl group and up to 16 glycol ether groups in the molecule.

Agent (b) can also include one or more zwitterionic surfactants such as, for example, betaines, N-alkyl-N,N-dimethylammonium glycinates, N-acyl-aminopropyl-N,N-dimethylammonium glycinates, and 2-alkyl-3-carboxymethyl-3-hydroxyethyl-imidazolines.

Agents (b) that are suitable according to the invention are further characterized in that agent (b) additionally includes at least one amphoteric surfactant. Preferred amphoteric surfactants are N-alkyl-glycines, N-alkylaminopropionic acids, N-alkylaminobutyric acids, N-alkyliminodipropionic acids, N-hydroxy-ethyl-N-alkylamidopropyl glycines, N-alkyl taurines, N-alkyl sarcosines, 2-alkylaminopropionic acids and alkylamino acetic acids. Especially preferred amphoteric surfactants are N-cocoalkyl-amino propionate, as cocoacylaminoethylaminopropionate and $C_{12}$-$C_{18}$ acyl sarcosine.

Moreover, it has proven advantageous if agent (b) includes other, non-ionogenic surface-active substances. Preferred nonionic surfactants are alkyl polyglycosides as well as alkylene oxide addition products to fatty alcohols, fatty acids and fatty acid glycerides, each with 2 to 50 mols of ethylene oxide per mol of fatty alcohol or fatty acid. Preparations with outstanding characteristics are also obtained if they include fatty acid esters of ethoxylated glycerin as nonionic surfactants. It is very especially preferred if agent (b) includes, as a nonionic surfactant, an ethoxylated castor oil with 2 to 50 mols of ethylene oxide per mol of fatty acid or an ethoxylated, hydrated castor oil with 2 to 50 mols of ethylene oxide per mol of fatty acid. The use of PEG-40 castor oil is especially preferred in this context. The nonionic, zwitterionic or amphoteric surfactants are used in proportions of 1.0 to 15.0 wt %, preferably 0.5 to 10.0 wt % and very especially preferably 0.7 to 5.0 wt % with respect to the total quantity of the agent.

To optimize the decolorizing effect, the ready-to-use decolorizing agent—i.e., the mixture of agents (a) and (b)—preferably has an acidic pH. Agent (b) is preferably set to an acidic pH of 1 to 6, preferably 1.3 to 4.5, more preferably 1.6 to 4.0 and especially preferably 2.0 to 3.6. To set the acidic pH, agent (b) preferably includes one or more organic and/or inorganic acids. A very especially preferred multi-component packaging unit (kit of parts) is further characterized in that the agent (b) in container (B) includes (b1) water and (b2) one or more acids from the group of the inorganic and/or organic acids.

One or more acids from the group of citric acid, tartaric acid, malic acid, lactic acid, acetic acid, sulfuric acid, hydrochloric acid, phosphoric acid, methanesulfonic acid, benzoic acid, malonic acid, oxalic acid, and/or 1-hydroxyethane-1,1-diphosphonic acid have proven to be particularly suitable. Malonic acid, oxalic acid and/or 1-hydroxyethane-1,1-diphosphonic acid are very especially preferably used.

A multi-component packaging unit (kit of parts) is therefore also especially preferred which is characterized in that the agent (b) in container (B) includes (b1) water and (b2) one or more acids from the group of citric acid, tartaric acid, malic acid, lactic acid, methanesulfonic acid, malonic acid, oxalic acid and/or 1-hydroxyethane-1,1-diphosphonic acid.

Agent (c) in Container (C)

The multi-component packaging unit according to the invention further comprises a third container (C) containing the separately packaged agent (c). Agent (c) is a post-treatment agent that is to be applied to the keratin fibers after the ready-to-use decolorizing agent (i.e., of the mixture of agents (a) and (b)) is applied, allowed to act, and preferably rinsed out.

Through the use of the post-treatment agent (c), the reoxidation and darkening is prevented that otherwise usually occurs any time the reductively treated, decolorized keratin fibers released by washing-out are exposed to the effect of atmospheric oxygen. In order to optimally prevent darkening, the post-treatment agent is preferably applied immediately after the decolorizing agent (i.e., the mixture of agents (a) and (b)) is rinsed out.

It is essential to the invention that agent (c) include at least one acid from the group of the inorganic and/or organic acids (c1) and at least one zwitterionic and/or amphoteric surfactant (c2). The ability to suppress reoxidation depends here substantially on the choice of the acid (c1) and of the amphoteric or zwitterionic (surfactant (c2). The two components (c1) and (c2) act together in preventing darkening, with special acids and select surfactants having proven to be especially effective.

In this connection, suitable acids are selected from the group consisting of citric acid, tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid and/or oxalic acid.

The acid or acids are used here both to set the pH that is optimal for the post-treatment agent (c) and to suppress darkening. The use of certain quantity ranges has proven especially expedient for solving the problem of the invention.

The acid or acids are preferably used in a total quantity of 2.0 to 20. wt %, preferably 3.0 to 18.0 wt %, more preferably 3.5 to 16.0 wt %, and especially preferably 4.0 to 14.0 wt % with respect to the total weight of the agent (c).

A preferred multi-component packaging unit (kit of parts) is further characterized in that the agent (c) in container (C) includes (c1) one or more acids from the group of citric acid, tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, and/or oxalic acid in a total quantity of 2.0 to 20.0 wt %, preferably 3.0 to 18.0 wt %, more preferably 3.5 to 16.0 wt %, and especially preferably 4.0 to 14.0 wt % with respect to the total weight of agent (c).

Acids that are selected from the group of methanesulfonic acid, malonic acid and/or oxalic acid have proven to be very especially effective. The acids methanesulfonic acid, malonic acid and oxalic acid are therefore again very especially preferred.

A very especially preferred multi-component packaging unit (kit of parts) is further characterized in that the agent (c) in container (C) includes (c1) one or more acids from the group of methanesulfonic acid, malonic acid and/or oxalic acid in a total quantity of 2.0 to 20.0 wt %, preferably 3.0 to 18.0 wt %, more preferably 3.5 to 16.0 wt %, and especially preferably 4.0 to 14.0 wt % with respect to the total weight of agent (c).

Over the course of the work leading to this invention, it was surprisingly found that the decolorizing result and its duration of effectiveness can be improved even further if the decolorizing agent (c) includes two different acids.

A very especially preferred multi-component packaging unit (kit of parts) is further characterized in that the agent (c) in container (C) (c1) includes oxalic acid and/or malonic acid as acids as well as another acid from the group of citric acid, tartaric acid, malic acid, lactic acid, acetic acid, hydroxyethane-1,1-diphosphonic acid, methanesulfonic acid, benzoic acid, hydrochloric acid, and sulfuric acid, phosphoric acid.

The very best decolorizing results were achieved with the acid mixtures oxalic acid/methanesulfonic acid and malonic acid/methanesulfonic acid.

An explicitly very especially preferred multi-component packaging unit (kit of parts) is further characterized in that the agent (c) in container (C) includes (c1) oxalic acid and/or malonic acid as acids as well as methanesulfonic acid as an additional acid.

As a second component that is essential to the invention, the agent (c) in container (C) includes one or more zwitterionic and/or amphoteric surfactants (c2).

Surfactants are understood as being amphiphilic (bifunctional) compounds with at least one hydrophobic residue and at least one hydrophilic moiety. The hydrophobic moiety is usually a hydrocarbon chain with about 10 to 30 carbon atoms.

In the case of the zwitterionic surfactants, the hydrophilic moiety comprises a zwitterionic structural unit, i.e., a structural unit that comprises both a cationically charged and an anionically charged moiety. Zwitterionic surfactants (c2) according to the invention are characterized in that they possess a cationically charged moiety in the form of a quaternary ammonium group and their anionic moiety is present in the form of a —COO— or —$SO_3^-$ group.

An ammonium group is quaternary is a grouping of the type $(R_1R_2R_3R_4N)^+$ is present, i.e., if all four H-atoms of the $NH_4$ ion from which the quaternary ammonium group is derived is replaced by organic residues R.

The —$SO_3^-$ group of the zwitterionic surfactant can be bonded directly to a carbon atom. In that case, the anionic portion of the zwitterionic compound is a deprotonated sulfonic acid group of the formula $R_5R_6R_7C$—$SO_3^-$, with the residues $R_5$, $R_6$, $R_7$ representing the remainder of the zwitterionic surfactant according to the invention.

However, it is also in keeping with the invention if the —$SO_3^-$ group is bonded via an oxygen atom to a carbon atom; in that case, the anionic part of the zwitterionic surfactant represents a deprotonated sulfuric acid ester of the formula $R_5R_6R_7C$—O—$SO_3^-$, and the residues $R_5$, $R_6$, $R_7$ again represent the remainder of the zwitterionic surfactant according to the invention.

It is preferred according to the invention if the —$SO_3^-$ group is bonded directly to a carbon atom, that is, if it is present in the form of a deprotonated sulfonic acid group.

Amphoteric surfactants are understood as being those surface-active compounds which, besides a $C_{10}$-$C_{30}$ alkyl or acyl group in the molecule, include at least one free amino group and at least one —COOH— or —$SO_3H$ group and are capable of forming inner salts. Examples of suitable amphoteric surfactants are N-alkylglycine, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylamino acetic acids, each with 10 to 30 C-atoms in the alkyl group. Especially preferred amphoteric surfactants are N-cocoalkylaminopropionate, as cocoacylaminoethylaminopropionate and $C_{12}$-$C_{18}$ acyl sarcosine.

Very especially preferably, the agent (c) includes one or more zwitterionic surfactants (c2). For this reason, a multi-component packaging unit (kit of parts) for the reductive decolorization of colored keratinic fibers is also very especially suitable which includes, packaged separately from one another, (I) a container (A) containing a cosmetic agent (a)
(II) a container (B) containing a cosmetic agent (b), and
(III) a container (C) containing a cosmetic, aqueous agent (c), with
  the agent (b) in container (B) including
  (a1) one or more reducing agents from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethane sulfinic acid, aminomethane sulfinic acid, cysteine, thiolactic acid, sulfanylacetic acid (thioglycolic acid) and/or ascorbic acid,
  the agent (b) in container (B) including
  (b1) water and
  (b2) one or more acids from the group of the inorganic and/or organic acids, and
  the agent (c) in container (C) including
  (c1) one or more acids from the group of the inorganic and/or organic acids and
  (c2) one or more zwitterionic surfactants.
The darkening of the decolorized keratin fibers was able to be prevented if one or more zwitterionic surfactants of formulas (I) to (IV) were used as the zwitterionic surfactant (c2) according to the invention,

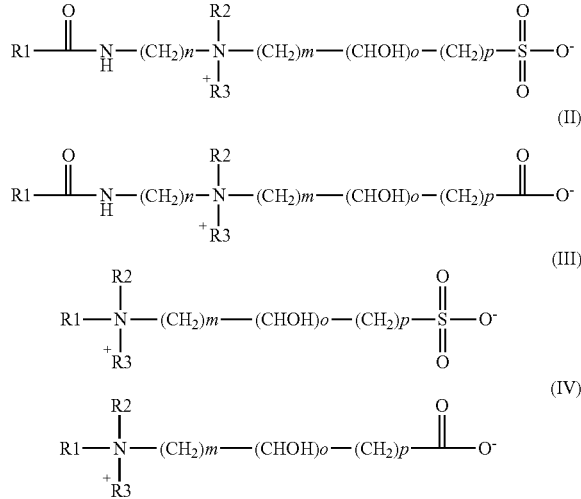

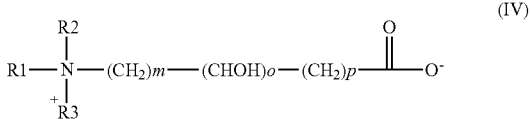

where
R1 each independently of one another, stands for a linear or branched $C_9$-$C_{29}$ alkyl group, a linear or branched $C_9$-$C_{29}$ alkenyl group or a linear or branched hydroxy-$C_9$-$C_{29}$ alkyl group,
R2, R3 each independently of one another, stand for a linear or branched $C_1$-$C_6$ alkyl group or a hydroxy-$C_2$-$C_6$ alkyl group,
n each independently of one another, stands for an integer from 1 to 6,
m each independently of one another, stands for an integer from 0 to 6,
o each independently of one another, stands for an integer from 0 to 6,
p each independently of one another, stands for an integer from 0 to 6, with the proviso that the sum of m, o and p be at least 1, respectively.

A preferred multi-component packaging unit (kit of parts) is further characterized in that the agent (c) in container (C) includes
(c2) one or more zwitterionic surfactants selected from the group of formulas (I) to (IV),

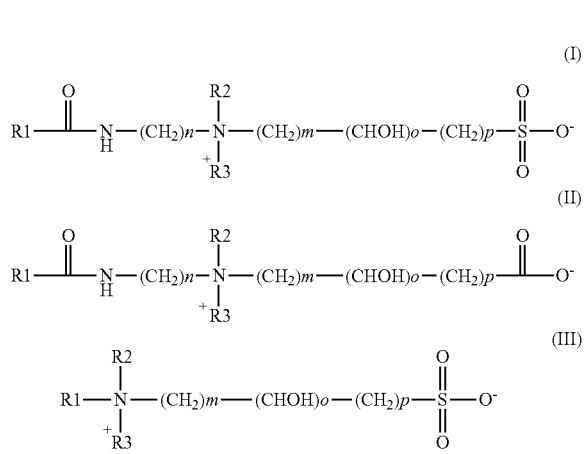

where
R1 each independently of one another, stands for a linear or branched $C_9$-$C_{29}$ alkyl group, a linear or branched $C_9$-$C_{29}$ alkenyl group or a linear or branched hydroxy-$C_9$-$C_{29}$ alkyl group,
R2, R3 each independently of one another, stand for a linear or branched $C_1$-$C_6$ alkyl group or a hydroxy-$C_2$-$C_6$ alkyl group,
n each independently of one another, stands for an integer from 1 to 6,
m each independently of one another, stands for an integer from 0 to 6,
o each independently of one another, stands for an integer from 0 to 6,
p each independently of one another, stands for an integer from 0 to 6, with the proviso that the sum of m, o and p be at least 1, respectively.

Within the group of the zwitterionic surfactants of formulas (I) to (IV), the surfactants of formulas (I) and/or (II) are very especially preferred.

Particularly preferably, zwitterionic surfactants of formula (I) are used in which the R1 residue stands for a linear $C_{11}$ alkyl group, a linear $C_{13}$ alkyl group, a linear $C_{15}$ alkyl group, a linear $C_{17}$ alkyl group or a linear $C_{19}$ alkyl group, a linear, monounsaturated $C_{11}$ alkenyl group, a linear, monounsaturated $C_{13}$ alkenyl group, a linear, monounsaturated $C_{15}$ alkyl group, a linear, monounsaturated $C_{17}$ alkenyl group or a linear, monounsaturated $C_{19}$ alkenyl group.

Furthermore, it is very especially preferred if n stands for the number 3.

Residues R2 and R3, preferably independently of one another, stand for a $C_1$-$C_6$ alkyl group, and R2 and R3 stand especially preferably for a methyl group.

n stands very especially preferably for the numbers 1 or 2.
o stands very especially preferably for the number 1.
p stands very especially preferably for the numbers 1 or 2.

A very especially preferred multi-component packaging unit (kit of parts) is further characterized in that the agent (c) in container (C) includes
(c2) one or more zwitterionic surfactants of formula (I),

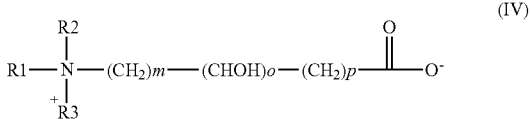

where
R1 stands for a linear or branched $C_{10}$-$C_{30}$ alkyl group or a linear or branched, mono- or polyunsaturated $C_{10}$-$C_{30}$ alkenyl group,
R2, R3 each independently of one another, stand for a $C_1$-$C_6$ alkyl group,
n stands for an integer from 1 to 6, preferably for the number 3,
m stands for an integer from 1 to 6,
o stands for an integer from 1 to 6, and
p stands for an integer from 1 to 6.

The zwitterionic surfactants of this very especially preferred type of formula (I) are also known by the name "amidopropyl hydroxysultaine." Laurylamidopropyl hydroxysultaine is a zwitterionic surfactant of formula (I), in which R1 stands for $C_{11}$ alkyl, R2 stands for methyl, R3 stands for methyl, n stands for 3, m stands for 1, o stands for 1 and p stands for 1.

Cocoamidopropyl hydroxysultaine represents a mixture of compounds of formula (I), in which R1 stands for $C_{11}$ alkyl to $C_{17}$ alkyl, R2 stands for methyl, n stands for 3, m stands for 1, o stands for 1 and p stands for 1.

Oleamidopropyl hydroxysultaine is a zwitterionic surfactant of formula (I), in which R1 stands for a monounsaturated $C_{17}$ alkenyl group (with the double bond lying between atoms 8 and 9 of the residue), R2 stands for methyl, R3 stands for methyl, n stands for 3, m stands for 1, o stands for 1 and p stands for 1. Cocoamidopropyl hydroxysultain, which is commercially available from Rhodia under the trade name Mirataine CBS, is explicitly very especially preferably used.

Another very especially preferred multi-component packaging unit (kit of parts) is characterized in that the agent (c) in container (C) includes (c2) one or more zwitterionic surfactants of formula (II),

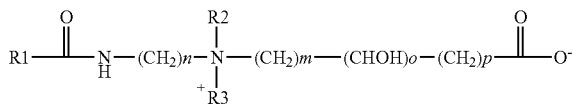

where
R1 stands for a linear or branched $C_9$-$C_{29}$ alkyl group or a linear or branched, mono- or polyunsaturated $C_9$-$C_{29}$ alkenyl group,
R2, R3 each independently of one another, stand for a $C_1$-$C_6$ alkyl group,
n stands for an integer from 1 to 6, preferably for the number 3,
m stands for an integer from 1 to 6,
o stands for 0, and
p stands for 0.

One example of an especially suitable zwitterionic surfactant of formula (II) is cocoamidopropyl betaine. Cocoamidopropyl betaine represents a mixture of compounds of formula (II), in which R1 stands for $C_{11}$ alkyl to $C_{17}$ alkyl, R2 stands for methyl, R3 stands for methyl, n is equal to 3, m is equal to 1, o is equal to 0 and p is equal to 0.

Another example of an especially suitable zwitterionic surfactant of formula (II) is lauramidopropyl betaine, in which R1 stands for $C_{11}$ alkyl, R2 stands for methyl, R3 stands for methyl, n is equal to 3, m is equal to 1, o is equal to 0 and p is equal to 0.

Together with the acids from group (c1), the use of the preferred and especially preferred inventive surfactants (c2) prevents darkening of decolorized strands, thereby ensuring a long-lasting decolorizing effect. It is especially advantageous in this regard to use surfactants in certain quantity ranges. It is especially preferred if agent (c) includes the zwitterionic and/or amphoteric surfactants (c2) in a total quantity of 3.0 to 50.0 wt %, preferably 5.0 to 40.0 wt %, more preferably 7.0 to 35.0 wt %, and especially preferably 7.5 to 25 wt % with respect to the total weight of agent (c).

A very especially preferred multi-component packaging unit (kit of parts) is further characterized in that the agent (c) in container (C) includes (c2) one or more zwitterionic and/or amphoteric surfactants in a total quantity of 3.0 to 50.0 wt %, preferably 5.0 to 40.0 wt %, more preferably 7.0 to 35.0 wt %, and especially preferably 7.5 to 25 wt % with respect to the total weight of agent (c).

Another especially preferred multi-component packaging unit (kit of parts) is further characterized in that the agent (c) in container (C) includes (c2) one or more zwitterionic surfactants in a total quantity of 3.0 to 50.0 wt %, preferably 5.0 to 40.0 wt %, more preferably 7.0 to 35.0 wt %, and especially preferably 7.5 to 25 wt % with respect to the total weight of agent (c).

Another especially preferred multi-component packaging unit (kit of parts) is further characterized in that the agent (c) in container (C) includes (c2) one or more amphoteric surfactants in a total quantity of 3.0 to 50.0 wt %, preferably 5.0 to 40.0 wt %, more preferably 7.0 to 35.0 wt %, and especially preferably 7.5 to 25 wt % with respect to the total weight of agent (c).

As described previously, it is very especially advantageous if zwitterionic surfactants are used as surfactants (c2). It is therefore especially preferred if agent (c) includes, as surfactants (c2), zwitterionic surfactants in a total quantity of 3.0 to 50.0 wt %, preferably 5.0 to 40.0 wt %, more preferably 7.0 to 35.0 wt %, and especially preferably 7.5 to 25 wt % with respect to the total weight of agent (c).

For this reason, a multi-component packaging unit (kit of parts) for the reductive decolorization of colored keratinic fibers is also very especially suitable which includes, packaged separately from one another, (I) a container (A) containing a cosmetic agent (a)
(II) a container (B) containing a cosmetic agent (b), and
(III) a container (C) containing a cosmetic, aqueous agent (c), with
    the agent (b) in container (B) including
    (a1) one or more reducing agents from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethane sulfinic acid, aminomethane sulfinic acid, cysteine, thiolactic acid, sulfanylacetic acid (thioglycolic acid) and/or ascorbic acid in a total quantity of 0.5 to 20.5 wt %, preferably 3.5 to 15.5 wt %, more preferably 6.0 to 13.5 wt %, and especially preferably 7.5 to 11.5 wt % with respect to the total weight of agent (a),
    the agent (b) in container (B) including
    (b1) water and
    (b2) one or more acids from the group of citric acid, tartaric acid, malic acid, lactic acid, methanesulfonic acid, malonic acid, oxalic acid and/or 1-hydroxyethane-1,1-diphosphonic acid,
    the agent (c) in container (C) including
    (c1) one or more acids from the group of citric acid, tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, and/or oxalic acid in a total quantity of 2.0 to 20.0 wt %, preferably 3.0 to 18.0 wt %, more preferably 4.0 to 16.0 wt %, and especially preferably 4.5 to 14.0 wt % with respect to the total weight of agent (c), and
    (c2) one or more zwitterionic surfactants in a total quantity of 3.0 to 50.0 wt %, preferably 5.0 to 40.0 wt %, more preferably 7.0 to 35.0 wt %, and especially preferably 7.5 to 25 wt % with respect to the total weight of agent (c).

The zwitterionic surfactant or surfactants (c2) are used together with acids (c1) in an aqueous cosmetic carrier, thus constituting the post-treatment agent (c) according to the invention. This agent (c) can be set to various pH values through the addition of acids and bases. The —COO⁻—SO$_3^-$ groups of the surfactants (c2) can also be partially protonated in the aqueous cosmetic carrier by changing the pH in an equilibrium reaction. These protonated forms of the zwitterionic surfactants are also included by this invention. All of the indicated quantities refer to the quantity of zwitterionic surfactants that are added in their zwitterionic form to the aqueous carrier.

The amphoteric surfactant or surfactants (c2) are also used together with acids (c1) in an aqueous cosmetic carrier, thus constituting the post-treatment agent (c) according to the invention in the context of this embodiment. This agent (c) can be set to various pH values through the addition of acids and bases. The —COOH—SO$_3$H groups of the amphoteric surfactants (c2) can also be partially deprotonated in the aqueous cosmetic carrier by changing the pH in an equilibrium reaction. Moreover, the protonatable groups present in the amphoteric surfactant (such as primary, secondary or tertiary amino groups, for example) can also be present in completely or partially protonated form as a function of the pH value present in the agent (c). All of these equilibrium reactions that the amphoteric surfactants can undergo during the setting of the pH value are likewise included by this invention. All of the indicated quantities refer to the quantity of amphoteric surfactants that are added in amphoteric form (acid group protonated, amino group not protonated) to the aqueous carrier.

Polyols

It was found that the use of polyols further supports the decolorizing effect. It is therefore preferred if the decolorizing agents according to the invention and/or the post-treatment agents according to the invention additionally include one or more polyols. A polyol is understood as being a compound with at least two aliphatic (i.e., non-phenolic) OH groups.

Examples of suitable polyols according to the invention are, in particular, ethylene glycol, 1,2-propylene glycol, 1,3-propanediol, 1,2-butanediol, 1,3-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol and 1,6-hexanediol. Polyethylene glycol and polypropylene glycol are also suitable, however.

In another preferred embodiment, a multi-component packaging unit (kit of parts) according to the invention is therefore characterized in that the agent (b) in container (B) additionally includes one or more polyols from the group of ethylene glycol (1,2-ethanediol), 1,2-propanediol, 1,3-propanediol, 1,2-butanediol, 1,3-butanediol, 1,4-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol, polyethylene glycol and/or polypropylene glycol. In another preferred embodiment, a multi-component packaging unit (kit of parts) according to the invention is therefore characterized in that the agent (c) in container (C) additionally includes one or more polyols from the group of ethylene glycol (1,2-ethanediol), 1,2-propanediol, 1,3-propanediol, 1,2-butanediol, 1,3-butanediol, 1,4-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol, polyethylene glycol and/or polypropylene glycol. The polyols are preferably contained in the agents according to the invention (agent (b) and/or agent (c)) in a total quantity of 0.5 to 15.0 wt %, preferably 1.0 to 11.5 wt %, more preferably 1.5 to 7.5 wt % and especially preferably 2.0 to 4.5 wt %—each with respect to the total weight of the agent in which the polyol or polyols are being used.

In another preferred embodiment, a multi-component packaging unit (kit of parts) according to the invention is therefore characterized in that the agent (b) in container (B) additionally includes one or more polyols from the group of ethylene glycol (1,2-ethanediol), 1,2-propanediol, 1,3-propanediol, 1,2-butanediol, 1,3-butanediol, 1,4-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol, polyethylene glycol and/or polypropylene glycol in a total quantity of 0.5 to 15.0 wt %, preferably 1.0 bis 11.5 wt %, more preferably 1.5 to 7.5 wt % and especially preferably 2.0 to 4.5 wt %—with respect to the total weight of the agent (a). In another preferred embodiment, a multi-component packaging unit (kit of parts) according to the invention is therefore characterized in that the agent (c) in container (C) additionally includes one or more polyols from the group of ethylene glycol (1,2-ethanediol), 1,2-propanediol, 1,3-propanediol, 1,2-butanediol, 1,3-butanediol, 1,4-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol, polyethylene glycol and/or polypropylene glycol in a total quantity of 0.5 to 15.0 wt %, preferably 1.0 bis 11.5 wt %, more preferably 1.5 to 7.5 wt % and especially preferably 2.0 to 4.5 wt % with respect to the total weight of the agent (c).

Other Surfactants

Besides the amphoteric and/or zwitterionic surfactants (b) that are essential to the invention, the post-treatment agents (c) according to the invention can also include other surfactants, such as nonionic and/or cationic surfactants, for example. It is preferred, however, if the agent (c) includes anionic surfactants only in small quantities. In this context, it is likewise preferred if the agents (a) and (b) also include the anionic surfactants only in small quantities. A "small quantity" is understood as referring to a quantity of less than 1 wt %, particularly a quantity of no more than 0.9 wt %, with the indicated quantity in percent by weight referring here to the total weight of the respective agent (a), (b) and (c).

In another preferred embodiment, a multi-component packaging unit according to the invention is therefore characterized in that the total quantity of all of the anionic surfactants contained in the agent (a) is no more than 0.9 wt %, preferably no more than 0.7 wt %, more preferably no more than 0.5 wt %, and especially preferably no more than 0.3 wt % with respect to the total weight of the agent (a), the total quantity of all of the anionic surfactants contained in the agent (b) is no more than 0.9 wt %, preferably no more than 0.7 wt %, more preferably no more than 0.5 wt %, and especially preferably no more than 0.3 wt % with respect to the total weight of the agent (b), and the total quantity of all of the anionic surfactants contained in the agent (c) is no more than 0.9 wt %, preferably no more than 0.7 wt %, more preferably no more than 0.5 wt %, and especially preferably no more than 0.3 wt % with respect to the total weight of the agent (c).

In terms of this invention, anionic surfactants are understood as being surfactants with an exclusively anionic charge.

Accordingly, it is preferred if the total quantity of all of the anionic surfactants contained in the agents (a), (b) and (c), respectively, from the group of the linear fatty acids with 10 to 22 C-atoms (soaps),
ether carboxylic acids of the formula R—O—($CH_2$—$CH_{2O}$)x —$CH_2$—COOH, in which R is a linear alkyl group with 10 to 22 C-atoms and x=0 or 1 to 16,
acyl sarcosides with 10 to 18 C-atoms in the acyl group,
acyl taurides with 10 to 18 C-atoms in the acyl group,
acyl isethionates with 10 to 18 C-atoms in the acyl group,
sulfosuccinic acid mono- and dialkyl esters with 8 to 18 C-atoms in the alkyl group and sulfosuccinic acid monoalkylpolyoxyethyl esters with 8 to 18 C-atoms in the alkyl group and 1 to 6 oxyethyl groups,
linear alkane sulfonates with 12 to 18 C-atoms,
linear alpha-olefin sulfonates with 12 to 18 C-atoms,
alpha-sulfo fatty acid methyl esters of fatty acids with 12 to 18 C-atoms, and
alkyl sulfates and alkyl polyglycol ether sulfates of the formula R—O($CH_2$—$CH_{2O}$)x-$SO_3$H, in which R is preferably a linear alkyl group with 10 to 18 C-atoms and x=0 or 1 to 12, is no more than 0.9 wt %, preferably no more than 0.7 wt %, more preferably no more than 0.5 wt %, and especially preferably no more than 0.3 wt % with respect to the total weight of the agent.

The agents (a), (b) and/or (c) can also include one or more nonionic surfactants. Nonionic surfactants are understood as being amphiphilic (bifunctional) compounds with at least one hydrophobic residue and at least one hydrophilic moiety. The hydrophobic moiety is usually a hydrocarbon chain with 10 to 30 carbon atoms. As a hydrophilic group, the nonionic surfactants carry a polyol group, a polyalkylene glycol ether group or a combination of polyol and polyglycol ether group. Such compounds are, for example, addition products of 2 to 30 mols of ethylene oxide and/or 0 to 5 mols of propylene oxide to linear fatty alcohols with 8 to 22 C-atoms, to fatty acids with 12 to 22 C-atoms and to alkyl phenols with 8 to 15 C-atoms in the alkyl group, $C_{12}$-$C_{22}$ fatty acid mono- and diesters of addition products of 1 to 30 mols of ethylene oxide to glycerin, $C_8$-$C_{22}$ alkyl mono- and oligoglycosides and ethoxylated analogs thereof as well as addition products of 5 to 60 mols of ethylene oxide to castor oil and hardened castor oil.

The additionally usable nonionic surfactants can be used in the agents (a), (b) and (c) according to the invention in a respective total quantity of 0.1 to 15.0 wt %, preferably 2.5 to 13.5 wt %, more preferably 3.5 to 11.5 wt %, and especially preferably 4.5 to 9.5 wt % with respect to the total weight of the respective agent.

According to the invention, the cationic surfactants used are particularly those of the type of the quaternary ammonium compounds, the esterquats, and the amidoamines. Preferred quaternary ammonium compounds are ammonium halogenides, particularly chlorides and bromides, such as alkyltrimethylammonium chlorides, dialkyldimethylammonium chlorides and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known by the INCI designations quaternium-27 and quaternium-83. The long alkyl chains of the abovementioned surfactants preferably have 10 to 18 carbon atoms.

Esterquats are known substances that include both at least one ester function and at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1,2-dihydroxypropyl dialkylamines. The alkylamido amines are usually manufactured by amidating natural or synthetic fatty acids and fatty acid cuts with dialkylamino amines. One compound from this group of substances that is especially suitable is stearamidopropyl dimethylamine, which is commercially available under the name Tegoamid® S 18. The quaternized protein hydrolysates represent other cationic surfactants that can be used according to the invention.

The additionally usable cationic surfactants can be used in the agents (a), (b) and (c) according to the invention in a respective total quantity of 0.1 to 15.0 wt %, preferably 2.5 to 13.5 wt %, more preferably 3.5 to 11.5 wt %, and especially preferably 4.5 to 9.5 wt % with respect to the total weight of the respective agent.

pH Values

As already described above, the decolorizing effect of the ready-to-use decolorizing agent is a function of the pH value, which passes through its optimum in the acidic pH range. Preferably, the ready-to-use decolorizing agent—i.e., the mixture of agents (a) and (b)—therefore has an acidic pH.

For stability-related reasons, it is preferred in the context of one embodiment if the agent (a) is tailored so as to be water-free.

Agent (b) can be particularly set at a pH of 1 to 6, preferably 1.3 to 4.5, more preferably 1.6 to 4.0, and especially preferably 2.0 to 3.6.

It was found that it is also advantageous if the decolorizing agent (c) is also acidic, since reoxidation or darkening is prevented especially well in this case.

For the abovementioned reasons, an especially preferred multi-component packaging unit (kit of parts) is further characterized in that the agent (a) in container (A) is a water-free agent,
the agent (b) in container (B) is an aqueous agent having a pH of 1 to 6, preferably 1.3 to 4.5, more preferably 1.6 to 4.0, and especially preferably 2.0 to 3.6 (measured using a Schott N61-type glass electrode at a temperature of 22° C.), and
the agent (c) in container (C) has a pH of 0.5 to 4.0, preferably 0.7 to 3.5, more preferably 0.9 to 3.0, and especially preferably 1.1 to 2.5 (measured using a Schott N61-type glass electrode at a temperature of 22° C.).

The pH values were measured using a Schott N61-type glass electrode at a temperature of 22° C.

In this context, "water-free" means that the agent (a) has a water content of no more than 10.0 wt %, preferably no more than 5.0 wt %, more preferably no more than 2.5 wt %, even more preferably no more than 1.0 wt %, and most preferably no more than 0.5 wt % with respect to the total weight of the agent (a).

In other words, a very especially preferred multi-component packaging unit (kit of parts) is further characterized in that the agent (a) in container (A) has a water content of no more than 10.0 wt %, preferably no more than 5.0 wt %, more preferably no more than 2.5 wt %, even more preferably no more than 1.0 wt %, and most preferably no more than 0.5 wt % with respect to the total weight of the agent (a), the agent (b) in container (B) is an aqueous agent having a pH of 1 to 6, preferably 1.3 to 4.5, more preferably 1.6 to 4.0, and especially preferably 2.0 to 3.6 (measured using a Schott N61-type glass electrode at a temperature of 22° C.), and the agent (c) in container (C) has a pH of 0.5 to 4.0, preferably 0.7 to 3.5, more preferably 0.9 to 3.0, and especially preferably 1.1 to 2.5 (measured using a Schott N61-type glass electrode at a temperature of 22° C.).

Although the pH value of the agents (b) and (c) preferably lies in the acidic range, the agents can include small quantities of alkalizing agents in order to fine-tune the pH value. The alkalizing agents that can be used according to the invention for this purpose can be selected from the group that is formed by ammoniac, alkanolamines, basic amino acids, as well as inorganic alkalizing agents such as alkaline (earth) metal hydroxides, alkaline (earth) metal silicates, alkaline (earth) metal phosphates, and alkaline (earth) metal hydrogen phosphates. Suitable inorganic alkalizing agents are sodium hydroxide, potassium hydroxide, sodium silicate and sodium metasilicate. Organic alkalizing agents that can be used according to the invention can be selected from among monoethanolamine, 2-amino-2-methylpropanol and triethanolamine. The basic amino acids that can be used as an alkalizing agent according to the invention can be selected from the group that is formed by arginine, lysine, ornithine and histidine.

Decolorization of Colored Keratin Fibers

The multi-component packaging unit according to the invention is a system comprising the agents (a), (b) and (c) that is used to decolorize previously colored keratinic fibers, particularly human hair. The colored keratin fibers are usually fibers that were previously colored using conventional oxidation dyes and/or direct dyes that are known to a person skilled in the art.

The decolorizing agents are suitable for removing colors that were produced on the keratin fibers using oxidation dyes based on developer and coupler components. If the following compounds were used as developers, the colors produced therewith were able to be removed using decolorizing agents well, effectively and nearly without subsequent darkening: p-phenylenediamine, p-toluylenediamineN,N-bis-(β-hydroxyethyl)-p-phenylenediamine, 4-N,N-Bis-(β-hydroxyethyl)-amino-2-methylaniline, 2-(β-hydroxyethyl)-p-phenylenediamine, 2-(a,β-dihydroxyethyl)-p-phenylenediamine, 2-hydroxymethyl-p-phenylenediamine, bis-(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/or 4,5-diamino-1-(β-hydroxyethyl)-pyrazole.

When the following compounds were used as couplers, the colors produced with them were also able to be removed with a very good decolorization result: m-phenylenediamine derivatives, naphthols, resorcinol and resorcinol derivatives, pyrazolones and m-aminophenol derivatives. Particularly suitable as couple substances are 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-pyrazolone-5, 2,4-dichloro-3-aminophenol, 1,3-bis-(2',4'-diaminophenoxy)-propane, 2-chloro-resorcinol, 4-chloro-resorcinol, 2-chloro-6-methyl-3-aminophenol, 2-amino-3-hydroxypyridine, 2-methylresorcinol, 5-methylresorcinol and 2-methyl-4-chloro-5-aminophenol.

1-naphthol, 1,5-dihydroxynaphthalene, 2,7-dihydroxynaphthalene, 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

The substrate to be decolorized can also have been colored using direct dyes. Direct dyes that merit consideration are particularly nitro-phenylenediamines, nitro-aminophenols, azo dyes, anthraquinones or indophenols. With the multi-component packaging unit (kit of parts) according to the invention, it is possible to decolorize keratin fibers, for example, that have been colored using the dyes and compounds known by the following international designations or trade names: HC yellow 2, HC yellow 4, HC yellow 5, HC yellow 6, HC yellow 12, acid yellow 1, acid yellow 10, acid yellow 23, acid yellow 36, HC orange 1, disperse orange 3, acid orange 7, HC red 1, HC red 3, HC red 10, HC red 11, HC red 13, acid red 33, acid red 52, HC red BN, pigment red 57:1, HC blue 2, HC blue 12, disperse blue 3, acid blue 7, acid green 50, HC violet 1, disperse violet 1, disperse violet 4, acid violet 43, disperse black 9, acid black 1, and acid black 52, as well as 1,4-diamino-2-nitrobenzene, 2-amino-4-nitrophenol, 1,4-bis-(β-hydroxyethyl)-amino-2-nitrobenzene, 3-nitro-4-(β-hydroxyethyl)-aminophenol, 2-(2'-hydroxyethyl)amino-4,6-dinitrophenol, 1-(2'-hydroxyethyl)amino-4-methyl-2-nitrobenzene, 1-Amino-4-(2'-hydroxyethyl)-amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

Moreover, the substrates to be decolorized can also be colored with naturally occurring dyes such as those contained, for example, in henna red, henna neutral, henna black, chamomile blossom, sandalwood, black tea, buckthorn bark, salvia, campeche wood, madder root, catechu, sedre and alkanet root.

The decolorizing agents according to the invention are conceived for the removal of these colorations and therefore preferably do not themselves include any dyes, that is, no developer-type or coupler-type oxidation dye precursors and no direct dyes.

In another preferred embodiment, a multi-component packaging unit (kit of parts) according to the invention is therefore characterized in that the total quantity of all of the dyes and oxidation dye precursors contained in the agent (a) is no more than 0.2 wt %, preferably no more than 0.1 wt %, more preferably no more than 0.05 wt %, and especially preferably no more than 0.01 wt % with respect to the total weight of the agent (a), the total quantity of all of the dyes and oxidation dye precursors contained in the agent (b) is no more than 0.2 wt %, preferably no more than 0.1 wt %, more preferably no more than 0.05 wt %, and especially preferably no more than 0.01 wt % with respect to the total weight of the agent (b), and the total quantity of all of the dyes and oxidation dye precursors contained in the agent (c) is no more than 0.2 wt %, preferably no more than 0.1 wt %, more preferably no more than 0.05 wt %, and especially preferably no more than 0.01 wt % with respect to the total weight of the agent (c).

Oxidizing Agents

The multi-component packaging unit according to the invention is used for the reductive decolorization of colored keratinic fibers. The agents (a) and (b) constitute together the ready-to-use decolorizing agent including a reducing agent.

For reasons of incompatibility, and to avoid exothermic, uncontrollable reactions, the agents (a) and (b) therefore preferably include no oxidizing agent.

The successive treatment of keratin fibers with reducing agents and oxidizing agents can result in very severe damage to the hair. In order to keep the damage to the keratin fibers to a minimum, it is therefore also preferred if the post-treatment agent (c) also does not include any oxidizing agent.

Oxidizing agents are understood here particularly as being oxidizing agents that can be used for oxidative decolorization, such as hydrogen peroxide and persulfates (potassium persulfate (alternatively potassium peroxodisulfate), sodium persulfate (sodium peroxodisulfate) and ammonium persulfate (alternatively ammonium peroxodisulfate)). It is therefore preferred that none of agents (a), (b) and (c) include the aforementioned oxidizing agents.

In another preferred embodiment, a multi-component packaging unit (kit of parts) according to the invention is therefore characterized in that the total quantity of all of the oxidizing agents from the group of the peroxides and the persulfates contained in the agent (a) is no more than 0.2 wt %, preferably no more than 0.1 wt %, more preferably no more than 0.05 wt %, and especially preferably no more than 0.01 wt % with respect to the total weight of the agent (a), the total quantity of all of the oxidizing agents from the group of the peroxides and the persulfates contained in the agent (b) is no more than 0.2 wt %, preferably no more than 0.1 wt %, more preferably no more than 0.05 wt %, and especially preferably no more than 0.01 wt % with respect to the total weight of the agent (b), the total quantity of all of the oxidizing agents from the group of the peroxides and the persulfates contained in the agent (c) is no more than 0.2 wt %, preferably no more than 0.1 wt %, more preferably no more than 0.05 wt %, and especially preferably no more than 0.01 wt % with respect to the total weight of the agent (c).

Mixing Ratio of Agents (a) and (b)

As already described above, the ready-to-use decolorizing agents are prepared by mixing agents (a) and (b). In principle, the agents (a) and (b) can be mixed in various mixing ratios, such as (a)/(b) from 20:1 to 1:20.

To ensure a comfortable mix, it can be advantageous to use the two agents (a) and (b) in approximately equal quantities. Particularly if acids are used in concentrated form in the agent (b), it can also be advantageous to use the agent (a) in surplus. However, if the agent (a) is formulated so as to be water-free, then it can also be advantageous on the other hand to use the agent (b) in surplus.

The agent (a) preferably includes the reducing agent or reducing agents (a1) in a total quantity of 25.0 to 100 wt %, preferably 45.0 to 100 wt %, more preferably 65.0 to 100 wt %, and especially preferably 85.0 to 100 wt % with respect to the total weight of agent (a). The reducing agent or reducing agents are therefore present in the agent (a) in relatively highly concentrated form.

Particularly if the reducing agents in these are also used in these concentration ranges in the agent (a), the use of a surplus of agent (b) is desirable.

In another preferred embodiment, a multi-component packaging unit according to the invention is therefore characterized in that the quantities of the agent (a) in container (A) and of the agent (b) in the container (B) are selected such that, during the preparation of the mixture for application—i.e., during the mixing of the agents (a) and (b)—the mixing ratio (a)/(b) is from 1:5 to 1:30.

In another especially preferred embodiment, a multi-component packaging unit according to the invention is therefore characterized in that the quantities of the agent (a) in container (A) and of the agent (b) in the container (B) are selected such that, during the preparation of the mixture for application—i.e., during the mixing of the agents (a) and (b)—the mixing ratio (a)/(b) is from 1:8 to 1:20, very especially preferably 1:10 to 1:15.

To prepare the mixture, the agent (a) can be transferred completely to container (B), which already includes the agent (b). In this case, the size of the container (B) is selected such that the container (B) can hold the total quantity of the agents (a) and (b) and also permits the mixing of the two agents (a) and (b), for example by shaking or stirring.

Analogously, the mixture can also be prepared by completely transferring the agent (b) from container (B) to container (A), which already includes the agent (a). In this case, the size of the container (A) should be selected such that the container (A) can hold the total quantity of the agents (a) and (b) and also permits the mixing of the two agents (a) and (b), for example by shaking or stirring.

Another possibility for the preparation of the mixture for application is the complete transfer of the two agents (a) and (b) from containers (A) and (B) into a third container, which then enables the mixing of the two agents—e.g., by shaking or stirring.

Example: A multi-component packaging unit according to the invention includes 10 g of sodium dithionite, agent (a) in container (A) (i.e., the total content of reducing agent(s) (a1) in agent (a) is 100 wt % (minus small impurities in the sodium dithionite)

100 g of agent (b) in container (B)

To prepare the mixture for application, the agent (a) is transferred completely from container (A) to container (B). The agents (a) and (b) are then shaken or stirred with one another. The mixing ratio of the agents (a)/(b) is from (10 g/100 g)=1:10.

Other Ingredients

Furthermore, the agents (a), (b) according to the invention can include other active substances, adjuvants and additives, such as, for example, nonionic polymers such as, for example, vinylpyrrolidone/vinyl acrylate copolymers, polyvinylpyrrolidone, vinylpyrrolidone/vinyl acetate copolymers, polyethylene glycols and polysiloxanes; additional silicones such as volatile or nonvolatile, straight-chain, branched or cyclic, crosslinked or non-crosslinked polyalkylsiloxanes (such as dimethicone or cyclomethicone), polyaryl siloxanes and/or polyalkylaryl siloxanes, particularly polysiloxane with organofunctional groups, such as substituted or unsubstituted amines (amodimethicone), carboxyl, Alkoxy and/or hydroxyl groups (dimethicone copolyols), linear polysiloxane(A)-polyoxyalkylene(B) block copolymers, grafted silicon polymers; cationic polymers such as quaternized cellulose ethers, polysiloxanes with quaternary groups, dimethyldiallyl ammonium chloride polymers, acrylamide dimethyldiallyl ammonium chloride copolymers, dimethylamino-ethylmethacrylate vinylpyrrolidone copolymers quaternized with diethyl sulfate, vinylpyrrolidone imidazolinium methochloride copolymers and quaternized polyvinyl alcohol; zwitterionic and amphoteric polymers; anionic polymers such as, for example, polyacrylic acids or crosslinked polyacrylic acids; structurants such as glucose, maleic acid and lactic acid, hair-conditioning compounds such as phospholipids, for example lecithin and cephaline; perfume oils, dimethyl isosorbide and cyclodextrins; fiber structure-improving active substances, particularly mono-, di- and oligosaccharides such as, for example, glucose, galactose, fructose, fruit sugar and lactose; colorants for coloring the agent; anti-dandruff agents such as piroctone olamine, zinc omadine and climbazol; amino acids and oligopeptides; animal- and/or plant-based protein hydrolysates, as well as in the form of their fatty acid condensation products or, optionally, anionically or cationically modified derivatives; plant oils; light stabilizers and UV blockers; active substances such as panthenol, pantothenic acid, pantolactone, allantoin, pyrrolidone carboxylic acids and salts thereof, as well as bisabolol; polyphenoles, particularly hydroxycinnamic acids, 6,7-dihydroxycoumarins, hydroxybenzoic acids, catechins, tannins, leucoanthocyanidins, anthocyanidins, flavanones, flavones and flavonols; ceramides or pseudo-ceramides; vitamins, provitamins and vitamin precursors; plant extracts; fats and waxes such as fatty alcohols, beeswax, montan wax and paraffins; swelling and penetration agents such as glycerin, propylene glycol monoethyl ethers, carbonates, hydrogen carbonates, guanidine, ureas as well as primary, secondary and tertiary phosphates; opacifiers such as latex, styrene/PVP and styrene/acrylamide copolymers; pearlescent agents such as ethylene glycol mono- and distearate as well as PEG-3 distearate; pigments, as well as propellants such as propane/butane mixtures, $N_2O$, dimethyl ether, $CO_2$ and air. Express reference is made in this connection to the known monographs, e.g., to Kh. Schräder, *Grundlagen and Rezepturen der Kosmetika* [Fundamentals and Formulations of Cosmetics], 2nd edition, Hüthig Buch Verlag, Heidelberg, 1989, which reflect the corresponding knowledge of a person skilled in the art.

Method

The previously described multi-component packaging units (kits of parts) according to the invention can be used in methods for reductive decolorization.

A second object of the present invention is therefore a method for the reductive decolorization of colored keratinic fibers comprising the following steps in the indicated sequence:
(I) Preparation of a ready-to-use decolorizing agent by mixing an agent (a) as defined in the description of the first object of the invention with an agent (b) as defined in the description of the first object of the invention,
(II) Application of the ready-to-use decolorizing agent on keratinic fibers,
(III) Allowing the decolorizing agent to act for a period of time of 5 to 60 minutes, preferably 10 to 55 minutes, more preferably 20 to 50 minutes, and especially preferably 30 to 45 minutes,
(IV) Rinsing of the decolorizing agent from the keratinic fibers, (V) Application of a cosmetic aqueous agent (c) as defined in the description of the first object of the invention to the keratinic fibers,
(VI) Allowing the agent (c) to act for a period of time of 30 seconds to 30 minutes, preferably 30 seconds to 20 minutes, more preferably 30 seconds to 10 minutes, and especially preferably 30 seconds to 5 minutes, and (VII) Rinsing of the agent (c) from the keratinic fibers.

Steps (I), (II), (III) and (IV) of the method constitute the decolorizing process for the keratin fibers and are therefore carried out in direct chronological sequence. In principle, there is no time-limit for the progression of steps (IV) and (V). Accordingly, step (V) can take place hours, days or even up to two weeks after conclusion of step (IV), for example. However, the method is intended to prevent the redarkening or reoxidation that can occur as a result of the effect of atmospheric oxygen on the decolorized keratin fibers. To effectively prevent this reoxidation, the post-treatment should take place before the atmospheric oxygen is able to act on the reduced keratin fibers over a long period of time. For this reason, the post-treatment should take place immediately after the decolorization if possible (i.e., right after the conclusion of method step (IV)). For this reason, it is preferred if a time period of no more than 12 hours, preferably no more than 6 hours, more preferably no more than 1 hour and especially preferably no more than 30 minutes passes between the conclusion of method step (IV) and the beginning of method step (V). A preferred method according to the invention is therefore characterized in that a time period of no more than 12 hours, preferably no more than 6 hours, more preferably no more than 1 hour and especially preferably no more than 30 minutes passes between method steps (IV) and (V).

The use of the post-treatment agent can also be repeated several times, for example if the agent (c) is a shampoo that is applied regularly after the decolorization. If the post-treatment (i.e., steps (V) to (VII)) is repeated, then it becomes possible to suppress the reoxidation for an especially long period of time.

An especially preferred method according to the invention is therefore characterized in that, following step (VII), the following steps are carried out in the indicated sequence:
(VIII) Application of a cosmetic aqueous agent (c) to the keratinic fibers, with the agent (c) being an agent as defined in the description of the first object of the invention,
(IX) Allowing the agent (c) to act for a period of time of 30 seconds to 30 minutes, preferably 30 seconds to 20 minutes, more preferably 30 seconds to 10 minutes, and especially preferably 30 seconds to 5 minutes, and
(X) Rinsing of the agent (c) from the keratinic fibers.

Steps (VIII) to (X) represent a repetition of the post-treatment with the agent (c); this post-treatment is performed following step (VII). In principle, there is no time-limit for the progression of steps (VII) and (VIII). For the sake of the user's comfort, however, it is preferred if the post-treatment with the agent (c) is carried out in the framework of the user's usual hair washing. For example, if the user normally washes his or her hair every one to two days, then the post-treatment agent (c) should be used for these hair washings. Accordingly, it is preferred if a time period of 12 to 48 hours, preferably 24 to 36 hours, elapses between steps (VII) and (VIII).

The method according to the invention is particularly effective for keratin fibers that were colored using certain oxidation dye precursors.

Above all, good results were achieved if the decolorization method was applied to keratin fibers that were colored with one or more oxidation dye precursors from the group of p-phenylenediamine, p-toluylenediamine, N,N-bis-(β-hydroxyethyl)-p-phenylenediamine, 2-(β-hydroxyethyl)-p-phenylenediamine and/or 2-(methoxymethyl)-p-phenylenediamine. A preferred method according to the invention is therefore further characterized in that the ready-to-use decolorizing agent is applied to keratin fibers that were colored with at least one oxidation dye precursor from the group of p-phenylenediamine, p-toluylenediamine, N,N-bis-(β-hydroxyethyl)-p-phenylenediamine, 2-(β-hydroxyethyl)-p-phenylenediamine and/or 2-(methoxymethyl)-p-phenylenediamine.

As regards other preferred embodiments of the method according to the invention, the remarks concerning the agents according to the invention apply mutatis mutandis.

EXAMPLES

1.1. Coloration

The following formulations were prepared (all information in wt %):

Coloring Cream (F1)

| Raw material | Wt % |
|---|---|
| Cetearyl alcohol | 8.5 |
| $C_{12}$-$C_{18}$ fatty alcohols | 3.0 |
| Ceteareth-20 | 0.5 |
| Ceteareth-12 | 0.5 |
| Plantacare 1200 UP (lauryl glucoside, 50-53% aqueous solution) | 2.0 |
| Sodium laureth-6 carboxylate (21% aqueous solution) | 10.0 |
| Sodium myreth sulfate (68-73% aqueous solution) | 2.8 |
| Sodium acrylate, trimethylammonium propyl acrylamide chloride copolymer (19-21% aqueous solution) | 3.8 |
| Potassium hydroxide | 0.83 |
| p-toluylenediamine, sulfate | 2.25 |
| m-aminophenol | 0.075 |
| 2-amino-3-hydroxypyridine | 0.12 |
| Resorcinol | 0.62 |
| 4-chlororesorcinol | 0.26 |
| 3-amino-2-methylamino-6-methoxypyridine | 0.04 |
| 1,3-bis(2,4-diaminophenoxy)propane, tetrahydrochloride | 0.05 |
| Ammonium sulfate | 0.1 |
| Sodium sulfite | 0.4 |
| Ascorbic acid | 0.1 |
| 1-hydroxyethane-1, 1-diphosphonic acid (60% aqueous solution) | 0.2 |
| Ammoniac (25% aqueous solution) | 7.2 |
| Water | Up to 100 |

Oxidizing Agent (Ox)

| Raw material | Wt % |
|---|---|
| Sodium benzoate | 0.04 |
| Dipicolinic acid | 0.1 |
| Disodium pyrophosphate | 0.1 |
| Potassium hydroxide | 0.09 |
| 1,2-propylene glycol | 1.0 |
| 1-hydroxyethane-1, 1-diphosphonic acid (60% aqueous solution) | 0.25 |
| Paraffinum liquidum | 0.30 |
| Steartrimonium chloride | 0.39 |
| Cetearyl alcohol | 3.4 |
| Ceteareth-20 | 1.0 |
| Hydrogen peroxide (50% aqueous solution) | 12.0 |

The coloring cream (F1) and the oxidizing agent (Ox) were mixed in a proportion of 1:1 and applied to strands of hair (Kerling natural European hair, white). The weight ratio of application mixture to hair was 4:1, and the exposure time was 30 minutes at a temperature of 32 degrees Celsius. The strands were then rinsed with water, dried, and allowed to sit for 24 hours at room temperature. The strands were colored in a dark-brown tone.

1.2 Decolorization

The following decolorizing agents were prepared (all information in wt % of active substance): Agent (a)

| Agent (a) | Wt % |
|---|---|
| Sodium dithionite | 8.8 |

Agent (b)

| Agent (b) | Wt % |
|---|---|
| Cetearyl alcohol | 2.9 |
| PEG-40 castor oil | 0.55 |
| Sodium cetearyl sulfate | 0.28 |
| Hydroxyethane-1,1-diphosphonic acid (1-etidronic acid) | 0.24 |
| Water (dest.) | up to 100 |
| pH value | 2.0 |

Agent (c)

| Agent (c) | (C1) | (C2) | (C3) | (C4) |
|---|---|---|---|---|
| Cocamidopropyl betaine | 11.4 | 11.4 | — | — |
| Cocamidopropyl | — | — | 12.5 | 12.5 |
| Oxalic acid | 4.5 | 4.5 | 4.5 | 4.5 |
| Methanesulfonic acid | — | 2.1 | — | 2.1 |
| PEG-12 dimethicone | 1.6 | 1.6 | 1.6 | 1.6 |
| Xanthan | 1.3 | 1.3 | 1.3 | 1.3 |
| Propylene glycol | 2.6 | 2.6 | 2.6 | 2.6 |
| Water | up to 100 | up to 100 | up to 100 | up to 100 |
| pH value | 2.0-2.4 | 2.0-2.4 | 2.0-2.4 | 2.0-2.4 |

Agents (a) and (b) were mixed (8.8 g of agent (a) were mixed with 100 g of agent (b)). This ready-to-use decolorizing agent was applied to the hairs colored under point 1.1 and allowed to act for 45 minutes at a temperature of 30° C.

The strands were then rinsed out with water for 20 seconds.

Immediately thereafter, the decolorized strands were treated with agent (c) for 1 minute and rinsed out again with water for 20 seconds. The treatment with agent (c) was repeated another two times. The strands were then rinsed out thoroughly with water for 5 minutes and dried.

The coloration of the strands was evaluated visually as a function of time. The evaluation of the color intensity was done based on the following scale:

0—Strand no longer has any perceptible coloration (white-blond, like the original coloration of the Kerling natural European hair white used)

1—Strand colored with low color intensity

2—Strand colored with medium color intensity

3—Strand colored with high color intensity

4—Coloration of the strand like immediately after coloration, no decolorizing effect A strand that was colored as described previously under point 1.1 was used as a reference (test V, comparison). Agents (a) and (b) were then mixed (8.8 g of agent (a) were mixed again with 100 g of agent (b)). This ready-to-use decolorizing agent was applied to the colored hairs and allowed to act for 45 minutes at a temperature of 30° C. The strands were then rinsed out with water for 5 minutes. The reference strand was therefore treated with the ready-to-use decolorizing agent ((a)+(b)) but not with the post-treatment agent (c). After decolorization (after the application of agent (a)+(b)), the strand was merely rinsed out thoroughly with water for a period of 5 minutes.

The coloration of the reference strand (test V, comparison) was also observed as a function of time.

The following results were obtained:

|  | V | (C1) | (C2) | (C3) | (C4) |
|---|---|---|---|---|---|
| Coloration of the strand during rinsing (5 minute) | 2-3 | 1-2 | 0-1 | 1-2 | 0-1 |
| Coloration of the strand after 10 minutes | 3 | 2 | 1 | 2 | 1 |
| Coloration of the strand after 60 minutes | 3 | 2 | 1 | 2 | 1 |
| Coloration of the strand after 1 day | 3-4 | 2 | 1 | 2 | 1 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A multi-component packaging unit (kit of parts) for the reductive decolorization of colored keratinic fibers comprising, packaged separately from one another,
   (I) a container (A) containing a cosmetic agent (a),
   (II) a container (B) containing a cosmetic agent (b), and
   (III) a container (C) containing a cosmetic, aqueous agent (c), with
      the agent (a) in container (A) comprising 85.0 to 100 wt % with respect to the total weight of agent (a), of
         (a1) one or more reducing agents selected from the group consisting of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethane sulfinic acid, aminomethane sulfinic acid, cysteine, thiolactic acid, sulfanylacetic acid (thioglycolic acid), ascorbic acid, and mixtures thereof,
      the agent (b) in container (B), comprises
         (b1) water and
         (b2) one or more acids selected from inorganic and/or organic acids, and
      agent (c) in container (C) comprising
         (c1) one or more acids selected from the group consisting of malonic acid, oxalic acid, and mixtures thereof, and
         (c2) methanesulfonic acid, wherein the total amount of the one or more acids (c1) and the methanesulfonic acid (c2) is present in agent (c) in a total quantity of 2.0 to 20.0 wt % with respect to the total weight of agent (c) and
         (c3) one or more zwitterionic and/or amphoteric surfactants
   wherein
      the agent (a) in container (A) is a water-free agent,
      the agent (b) in container (B) is an aqueous agent having a pH of 1 to 6, measured using a Schott N61-type glass electrode at a temperature of 22° C.,
   and
      the agent (c) in container (C) has a pH of 0.5 to 4.0 measured using a Schott N61-type glass electrode at a temperature of 22° C.

2. The multi-component packaging unit (kit of parts) according to claim 1, wherein
   the agent (a) in container (A) comprises
      (a1) one or more reducing agents selected from the group consisting of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, and mixtures.

3. The multi-component packaging unit (kit of parts) according to claim 1, wherein the total amount of the one or more acids (c1) and the methanesulfonic acid (c2) is present in agent (c) in a total quantity of 4.0 to 14.0 wt % with respect to the total weight of agent (c).

4. The multi-component packaging unit (kit of parts) according to claim 1, wherein
   the agent (c) in container (C) comprises
      (c3) one or more zwitterionic surfactants selected from the group of formulas (I) to (IV),

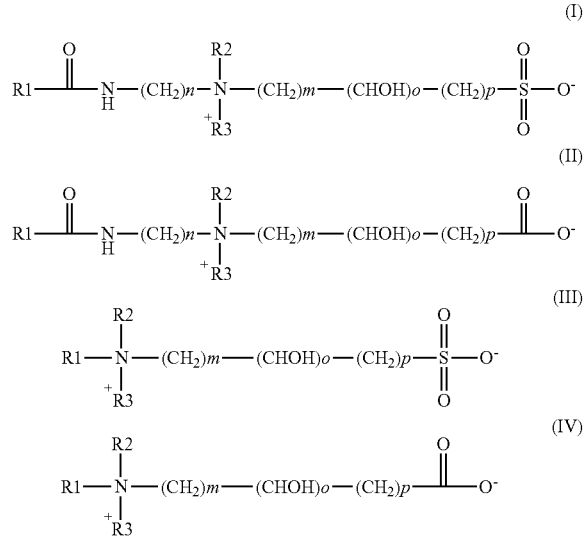

where
   R1 each independently of one another, stands for a linear or branched $C_9$-$C_{29}$ alkyl group, a linear or branched $C_9$-$C_{29}$ alkenyl group or a linear or branched hydroxy-$C_9$-$C_{29}$ alkyl group,
   R2, R3 each independently of one another, stand for a linear or branched $C_1$-$C_6$ alkyl group or a hydroxy-$C_2$-$C_6$ alkyl group,
   n each independently of one another, stands for an integer from 1 to 6,
   m each independently of one another, stands for an integer from 0 to 6,
   o each independently of one another, stands for an integer from 0 to 6,
   p each independently of one another, stands for an integer from 0 to 6, with the proviso that the sum of m, o and p be at least 1.

5. The multi-component packaging unit (kit of parts) according to claim 1, wherein the agent (c) in container (C) comprises
(c3) one or more zwitterionic surfactants of formula (I),

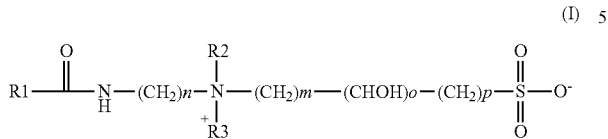

where
R1 stands for a linear or branched $C_{10}$-$C_{30}$ alkyl group or a linear or branched, mono- or polyunsaturated $C_{10}$-$C_{30}$ alkenyl group,
R2, R3 each independently of one another, stand for a $C_1$-$C_6$ alkyl group,
n stands for an integer from 1 to 6,
m stands for an integer from 1 to 6,
o stands for an integer from 1 to 6, and
p stands for an integer from 1 to 6.

6. The multi-component packaging unit (kit of parts) according to claim 1, wherein
the agent (c) in container (C) comprises
(c3) one or more zwitterionic surfactants of formula (II),

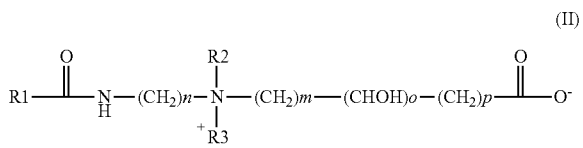

where
R1 stands for a linear or branched $C_9$-$C_{29}$ alkyl group or a linear or branched, mono- or polyunsaturated $C_9$-$C_{29}$ alkenyl group,
R2, R3 each independently of one another, stand for a $C_1$-$C_6$ alkyl group,
n stands for an integer from 1 to 6,
m stands for an integer from 1 to 6,
o stands for 0, and
p stands for 0.

7. The multi-component packaging unit (kit of parts) according to claim 1, wherein
the agent (c) in container (C) includes
(c3) one or more zwitterionic and/or amphoteric surfactants in a total quantity of 3.0 to 50.0 wt % with respect to the total weight of agent (c).

8. The multi-component packaging unit (kit of parts) according to claim 1, wherein
the total quantity of all of the dyes and oxidation dye precursors included in the agent (a) is no more than 0.2 wt %, with respect to the total weight of the agent (a),
the total quantity of all of the dyes and oxidation dye precursors included in the agent (b) is no more than 0.2 wt %, with respect to the total weight of the agent (b), and
the total quantity of all of the dyes and oxidation dye precursors included in the agent (c) is no more than 0.2 wt %, with respect to the total weight of the agent (c).

9. The multi-component packaging unit (kit of parts) according to claim 1, wherein
the total quantity of all of the oxidizing agents from the group of the peroxides and the persulfates included in the agent (a) is no more than 0.2 wt %, with respect to the total weight of the agent (a),
the total quantity of all of the oxidizing agents from the group of the peroxides and the persulfates included in the agent (b) is no more than 0.2 wt %, with respect to the total weight of the agent (b),
the total quantity of all of the oxidizing agents from the group of the peroxides and the persulfates included in the agent (c) is no more than 0.2 wt %, with respect to the total weight of the agent (c).

10. A method for the reductive decolorization of colored keratinic fibers comprising the following steps in the indicated sequence:
(I) preparation of a ready-to-use decolorizing agent by mixing an agent (a) according to claim 1 with an agent (b) according to claim 1,
(II) applying the ready-to-use decolorizing agent on keratinic fibers,
(III) allowing the decolorizing agent to act for a period of time of 5 to 60 minutes,
(IV) rinsing of the decolorizing agent from the keratinic fibers,
(V) applying a cosmetic aqueous agent (c) according to claim 1,
(VI) allowing the agent (c) to act for a period of time of 30 seconds to 30 minutes, and
(VII) rinsing of the agent (c) from the keratinic fibers.

11. The method according to claim 10, wherein, following step (VII), the following steps are carried out in the indicated sequence:
(VIII) applying a cosmetic aqueous agent (c) to the keratinic fibers,
(IX) allowing the agent (c) to act for a period of time of 30 seconds to 30 minutes, and
(X) rinsing of the agent (c) from the keratinic fibers.

12. The method according to claim 10, wherein
the ready-to-use decolorizing agent is applied to keratin fibers that were colored with at least one oxidation dye precursor from the group of p-phenylenediamine, p-toluylenediamine, N,N-bis-(β-hydroxyethyl)-p-phenylenediamine, 2-(β-hydroxyethyl)-p-phenylenediamine and/or 2-(methoxymethyl)-p-phenylenediamine.

* * * * *